(12) United States Patent
Berry

(10) Patent No.: US 6,543,138 B1
(45) Date of Patent: Apr. 8, 2003

(54) METHOD AND APPARATUS FOR SECURING DRIP IRRIGATION TUBING TO CONNECTOR

(76) Inventor: Robert J. Berry, P.O. Box 6122 — 6801 E. Stagecoach Pass, Carefree, AZ (US) 85377

(*) Notice: Subject to any disclaimer, the term of this patent is extended or adjusted under 35 U.S.C. 154(b) by 0 days.

(21) Appl. No.: 09/991,587

(22) Filed: Nov. 23, 2001

(51) Int. Cl.[7] .................................................. B21K 1/16
(52) U.S. Cl. .............................. 29/890.144; 29/890.14; 29/451; 285/242
(58) Field of Search ................ 29/890.14, 890.144, 29/890.148, 890.149, 450, 451, 453, 525.01, 237, 890.141, 525, 525.05; 285/242, 252, 321, 5; 403/278, 279, 281, 282

(56) References Cited

U.S. PATENT DOCUMENTS

| | | | | |
|---|---|---|---|---|
| 367,790 A | * | 8/1887 | Darrah, Jr. | |
| 2,433,602 A | * | 12/1947 | Coss | |
| 3,484,121 A | * | 12/1969 | Quinton | |
| 3,674,292 A | * | 7/1972 | Demler, Sr. | |
| 4,313,629 A | * | 2/1982 | Winterhalter | |
| 4,564,222 A | * | 1/1986 | Loker et al. | |
| 4,693,707 A | * | 9/1987 | Dye | |
| 4,790,569 A | * | 12/1988 | Chaffee | |
| 5,607,190 A | * | 3/1997 | Exandier et al. | |
| 5,735,554 A | * | 4/1998 | Imgam | |
| 6,003,906 A | * | 12/1999 | Fogarty et al. | |
| 6,231,085 B1 | * | 5/2001 | Olson | |
| 6,270,125 B1 | * | 8/2001 | Rowley et al. | |

* cited by examiner

Primary Examiner—Gregory M. Vidovich
Assistant Examiner—T. Nguyen
(74) Attorney, Agent, or Firm—Tod R. Nissle, P.C.

(57) ABSTRACT

A method and apparatus for assembling a drip irrigation system includes a drip irrigation member with a connector and includes a length of tubing. The tubing has an end. A securing member is mounted on the end of the tubing. The end is slidably forced over the connector. The securing member is rolled along the tubing to a position at which the securing member elastically circumferentially compresses the tubing against the connector.

2 Claims, 3 Drawing Sheets

METHOD AND APPARATUS FOR SECURING DRIP IRRIGATION TUBING TO CONNECTOR

This invention pertains to drip irrigation tubing.

More particularly, this invention pertains to a method and apparatus for securing an end of drip irrigation tubing to a connector.

Drip irrigation systems are well known in the art, particularly in the desert southwest of the United States and other arid areas. One well known system utilizes lengths of black plastic tubing. The tubing is pliable but is also somewhat rigid. Short lengths of the tubing about one inch long often are difficult to bend through a ninety degree angle without crimping the tube. The drip irrigation system also includes connectors for fastening together lengths of tubing and for attaching the end of a piece of tubing to a nozzle. Each connector typically comprises a hollow, tapered, conically shaped member. The small tapered end of the connector has an outer diameter about equal to the inner diameter of the black drip irrigation tubing. The larger end of the connector has an outer diameter greater than the inner diameter of the black drip irrigation tubing. When the end of the tubing is slid over the connector, the larger end of the connector causes the tubing to elastically expand. Such expansion of the black tubing holds the tubing on the connector and also forms a seal between the larger end of the connector and the inner cylindrical surface of the black plastic tubing.

A long existing problem associated with such a system is that, over time, the black tubing loses it elasticity, becomes loose on the connector, and eventually separates from the connector. The pressure of water in the tubing facilitates the separation of the end of the black tubing from the connector. In particular, variations in water pressure facilitate the separation of the tubing from the connector. Another important factor is the summer heat. Summer heat softens the tubing and accelerates the degradation of the tubing. This is especially the case in warm climates where summer temperatures regularly exceed 100 degrees F. Once the end of the black tubing separates from the connector, the end of the tubing can sometimes be cut off to produce a new end which has sufficient elasticity to engage sealingly the conical end of the connector. This procedure is sometimes only a short-lived fix because the elasticity of the entire length of the tubing has often degraded over time.

Accordingly, it would be highly desirable to provide an improved method and apparatus which would sealingly engage the end of a drip irrigation tubing to a connector even after the tubing lost its elasticity.

Therefore, it is a principal object of the invention to provide an improved drip irrigation system.

Another object of the invention is to provide an improved method and apparatus for sealingly engaging a connector with the end of a length of drip irrigation tubing.

A further object of the invention is to provide an improved method and apparatus of the type described which does not require tools and can be utilized by an individual with limited manual strength and dexterity.

Still another object of the invention is to provide an improved method and apparatus of the type described which can be utilized repeatedly at minimal expense during the life of a connector and of a piece of drip irrigation tubing attached to the connector.

These and other, further and more specific objects and advantages of the invention will be apparent from the following detailed description of the invention, taken in conjunction with the drawings, in which.

Figure 1:
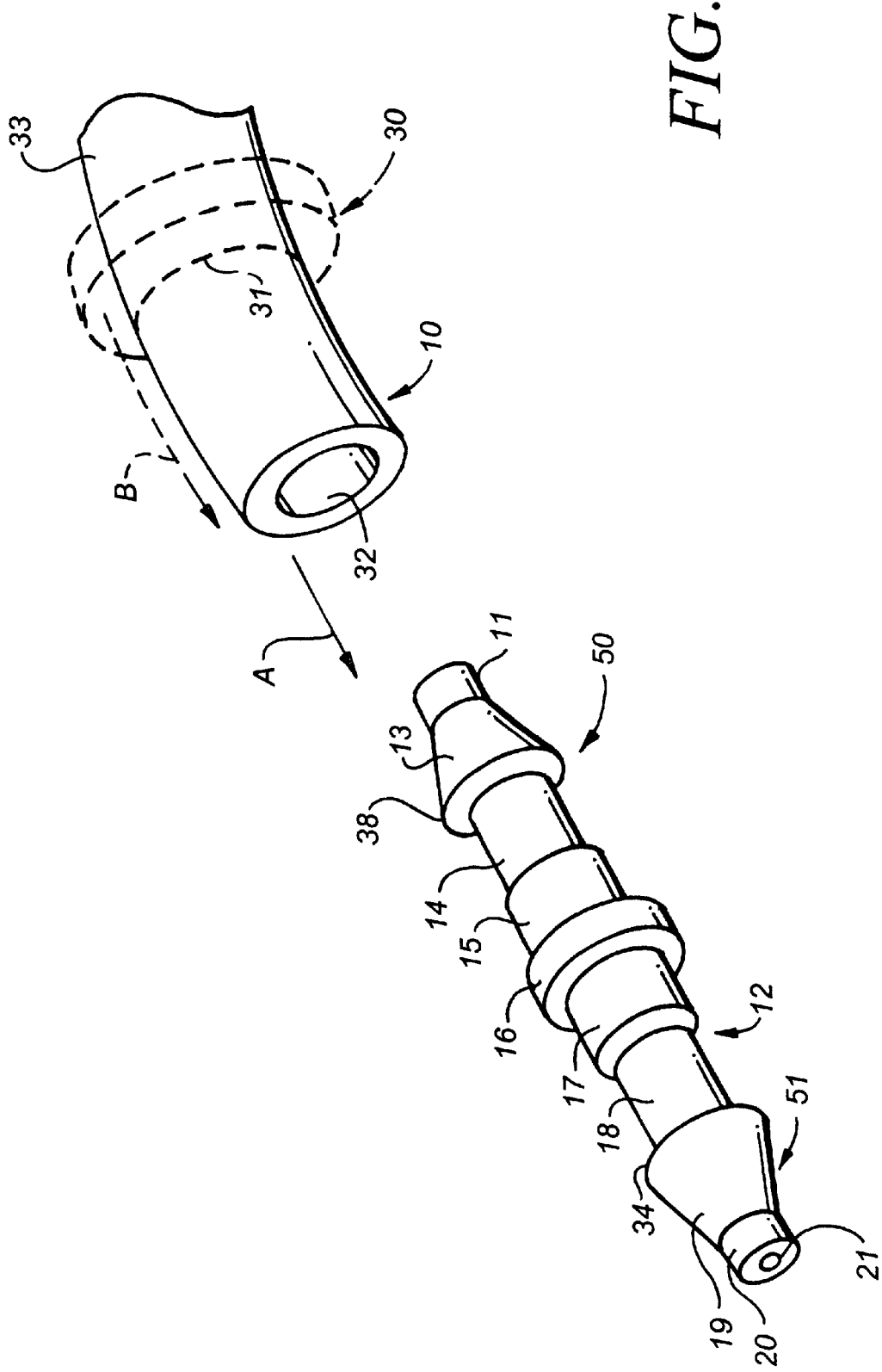
FIG. 1 is perspective exploded view illustrating a drip irrigation connector, an end of a length of drip irrigation tubing, and a securing apparatus utilized in accordance with the invention.

Briefly, in accordance with my invention, I provide an improved method for assembling a drip irrigation system. The method includes the steps of providing a length of elastic hollow pliable drip irrigation tubing having first and second ends and an inner cylindrical surface with a selected diameter along the length of the tubing and having an outer cylindrical surface with a selected outer diameter; providing a hollow drip irrigation member including at least a first end and a second end, the first end of the member including a connector, the connector being shaped and dimensioned to include a portion having a width greater than the inner diameter of the tubing to expand the inner cylindrical surface of the drip irrigation tubing to a width greater than the inner diameter when the inner cylindrical surface is slidably forced over the connector; providing an elastic member with an opening formed therethrough, the opening having a width less than the outer diameter of the tubing such that when the tubing is inserted through the opening, the tubing elastically expands the member so that the diameter of the opening is equivalent to the outer diameter; inserting the tubing through the opening of the elastic member to mount the elastic member on the end of the tubing; and, slidably forcing the end of the tubing over the connector.

In another embodiment of the invention, I provide an improved method for assembling a drip irrigation system. The method includes the steps of providing a length of elastic hollow pliable drip irrigation tubing having first and second ends and an inner cylindrical surface with a selected diameter along the length of the tubing and having an outer cylindrical surface with a selected outer diameter; providing a hollow drip irrigation member including at least a first end and a second end, the first end of the member including a connector, the connector being shaped and dimensioned to include a portion having a width greater than the inner diameter of the tubing to expand the inner cylindrical surface of the drip irrigation tubing to a width greater than the inner diameter when the inner cylindrical surface is slidably forced over the connector; providing an elastic member with an opening formed therethrough, the opening having a width less than the outer diameter of the tubing such that when the tubing is inserted through the opening, the tubing elastically expands the opening, the elastic member being shaped to roll along the tubing when the elastic member is pushed along on the tubing; inserting the tubing through the opening of the elastic member to mount the elastic member on the tubing; slidably forcing the end of the tubing over the connector; and, rolling the elastic member along the tubing to a selected position on the tubing where the tubing circumscribes the connector.

In a further embodiment of the invention, I provide an improved method for assembling a drip irrigation system. The method includes the steps of providing a length of elastic hollow pliable drip irrigation tubing having first and second ends and an inner cylindrical surface with a selected diameter along the length of the tubing and having an outer cylindrical surface with a selected outer diameter; providing a hollow drip irrigation member including at least a first end and a second end, the first end of the member including a connector, the connector being shaped and dimensioned to include a portion having a width greater than the inner diameter of the tubing to expand the inner cylindrical surface of the drip irrigation tubing to a width greater than the inner diameter when the inner cylindrical surface is slidably forced over the connector; providing a securing member shaped and dimensioned to be mounted on the tubing and circumferentially generally uniformly apply a compressive force to the outer surface of the tubing; slidably forcing the end of the tubing over the connector; and, mounting the securing member on the end of the tubing to compress circumferentially the end of the tubing against the connector.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates an exploded view of a drip irrigation member 12 and the end of a length of pliable elastic tubing 10. Tubing 10 includes an inner cylindrical surface 32 having a diameter and includes an outer surface 33 having a diameter indicated by arrows G in FIG. 3. While the size of drip irrigation tubing can vary as desired, one common size of tubing 10 has an outer diameter (cylindrical outer surface 33) of about one-quarter inch and an inner diameter (cylindrical inner surface 32) of about 5/32 of an inch.

Drip irrigation member 12 includes a central portion including interconnected hollow cylindrical members 15, 16, 17. A connector is attached to each side of the central portion. One connector 50 is attached to member 15 and includes hollow cylindrical tip 11, hollow conical member 13, and hollow cylindrical member 14 connected to member 15. Member 13 includes circular lip 38. Lip 38 has a diameter greater than the diameter of surface 32. The other connector 51 is attached to member 17 and includes hollow cylindrical tip 20, hollow conical member 19, and hollow cylindrical member 18 connected to member 17. Member 19 includes circular lip 34. Lip 34 has a diameter equal to the diameter of lip 38. Cylindrical aperture 21 extends the length of member 12 and extends through tip 20, members 14 to 19, and tip 11. Aperture 21 is the "hollow" portion of tip 20, members 14 to 19, and tip 11. Member 12 can be fabricated in any desired manner, but typically is molded as a unitary integrated piece. Tips 11 and 20 each have an outer diameter equal to or slightly less than the diameter of inner surface 32 of tubing 10.

Member 12 need only, if desired, have one connector. The other connector can be replaced with a nozzle which permits water flowing into member 12 from tubing 10 to flow out of member 12. The shape and dimension of member 12 can be varied as desired. For example, member 12 can have a "T" shaped such that ithas three separate ends on which tubing 10 can be slidably mounted.

When elastic, pliable doughnut shaped securing member 30 is mounted on tubing 10 in the manner illustrated in FIGS. 1 to 4, member 30 has an elastically expanded inner diameter 31 equivalent to the outer diameter of surface 33. When member 30 is not mounted on tubing 10, member 30 elastically contracts to its normal doughnut shape in which the inner diameter 31 is less than the outer diameter of surface 33. Member 30 functions to circumferentially generate compressive forces against tubing 10 when member 30 is mounted on tubing 10 in the manner shown in FIGS. 1 to 4. These compressive forces are generated because, as noted, opening 31 is elastically expanded when member 30 is mounted on tubing 10. Accordingly, member 30 is attempting to contract elastically to its original "reduced-size" doughnut shape whenever member 30 is mounted on tubing 10 in the manner illustrated in FIGS. 1 to 4. This attempt to elastically contract generates forces around the circumference of tubing 10 (at points where member 30 contacts surface 33) which are generally of uniform strength or magnitude at each point at which member 30 circumferentially contacts tubing 10. Member 30 must generally uniformly compress tubing 10 around the entire circumference, otherwise a leak can develop at points where tubing 10 is not compressed by member 30 against the connector 50.

Elastic member 30 can be fabricated from any desired material. Member 30 must, however, have an opening 31 which has a diameter smaller than the diameter of tubing 10. For example, if tubing 10 has an outer diameter of one-quarter inch, the diameter of opening 31 (before member 30 is mounted on tubing 10) is presently about 5/32 inch. Opening 31 elastically stretches to a diameter of one-quarter inch when member 30 is mounted on tubing 10.

Member 30 must be elastic and attempt to return to its original shape and dimension after member 30 is mounted on tubing 10. This elasticity generates the compressive forces necessary in the practice of the invention.

Member 30 is presently comprised of latex, another rubber, an elastic plastic, or other elastomer which preferably, but not necessarily, has a durometer in the range of ten to forty. While durometers greater than forty can be utilized, they are not preferred because the latex becomes so stiff that it is difficult to stretch it to increase the size of opening 31 when member 30 is mounted on tubing 10. One of the virtues of the invention is that member 30 can readily manually be mounted on tubing 10. If the durometer is too high, this also interferes with the ability of member 30 to roll in the manner described below. The rolling application of member 30 also facilitates its manual application to member 10. If the durometer is less than ten, it becomes increasingly soft and the compressive forces applied to tubing 10 decrease The ability of member 30 to roll along tubing 10 is important in the method of the invention because it facilitates mounting of member 30 on tubing 10. If member 30 cannot roll, then it must either be slid along surface 33 or a tool must be utilized to position member 30 on tubing 10. Sliding member 30 along surface 33 is usually possible, but compressive forces—for example, the forces indicated by arrows P and Q in FIG. 2—generated against surface 33 by member 30 create frictional forces between member 30 and surface 33 which impede the sliding of member 30 along surface 33.

Figure 3:
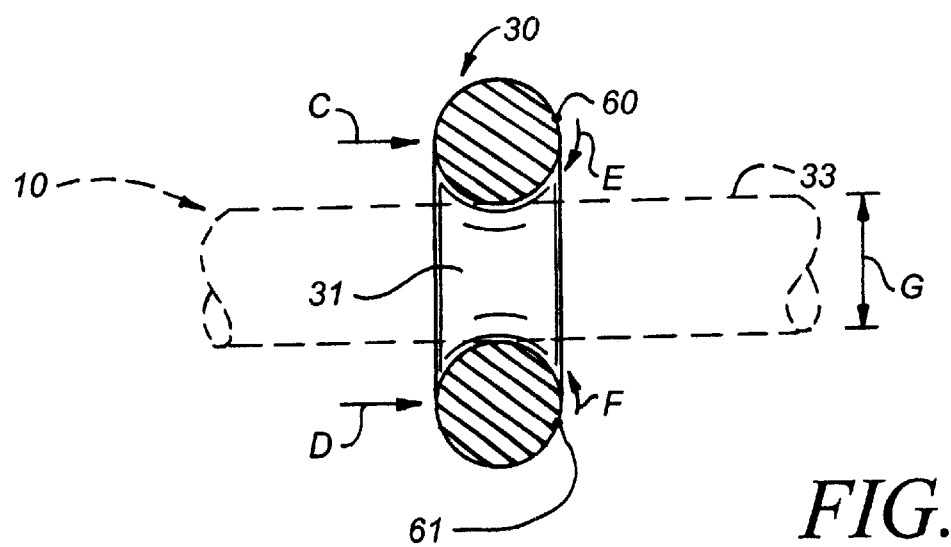
FIG. 3 is a side section view illustrating the mode of operation of a securing apparatus utilized in accordance with the invention; and, FIG. 4 is a side view further illustrating the mode of operation of a securing apparatus utilized in the invention.

The rolling ability of member 30 is illustrated in FIG. 3. When a user's fingers press against member 30 in the direction of arrows C and D, member 30 rolls along surface 33 of tube 10 such that point 60 moves downwardly and inwardly in the direction of arrow E, and point 61 moves upwardly and inwardly in the direction of arrow F. After member 30 makes one completed revolution while moving along tube 10 in the direction of arrows C and D, points 60 and 61 return to the positions shown in FIG. 3.

Figure 4:
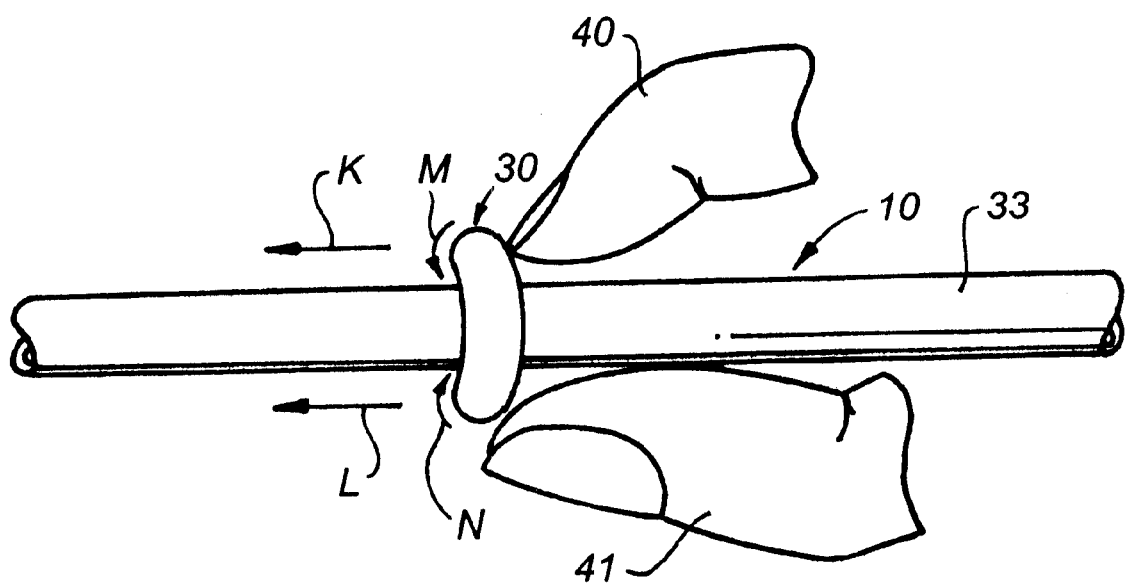

FIG. 4 further illustrates member 30 being pushed along tubing 10 by the index finger 40 and thumb 41 of the user's right hand. The index finger 40 pushes the upper part of member 30 in the direction indicated by arrow K. The thumb 41 pushes the lower part of member 30 in the direction indicated by arrow L. As member 30 moves in the directions indicated by arrows K and L, member 30 rolls along surface 33 in the manner indicated by arrows M and N. The frictional engagement between surface 33 and the inner portion of member 30 facilitates the rolling of member 30 along surface 33. Since member 30 is elastic, when finger 40 and thumb 41 begin to push on member 30, member 30 tends to bow as illustrated in FIG. 4 before member 30 beings to roll along tubing 10. The ability of member 30 to roll along tubing 10 simplifies installation of member 30 on tubing 10 because it takes less effort to roll member 30 along tubing 10 than to attempt to slide member 30 along tubing 10.

Figure 2:
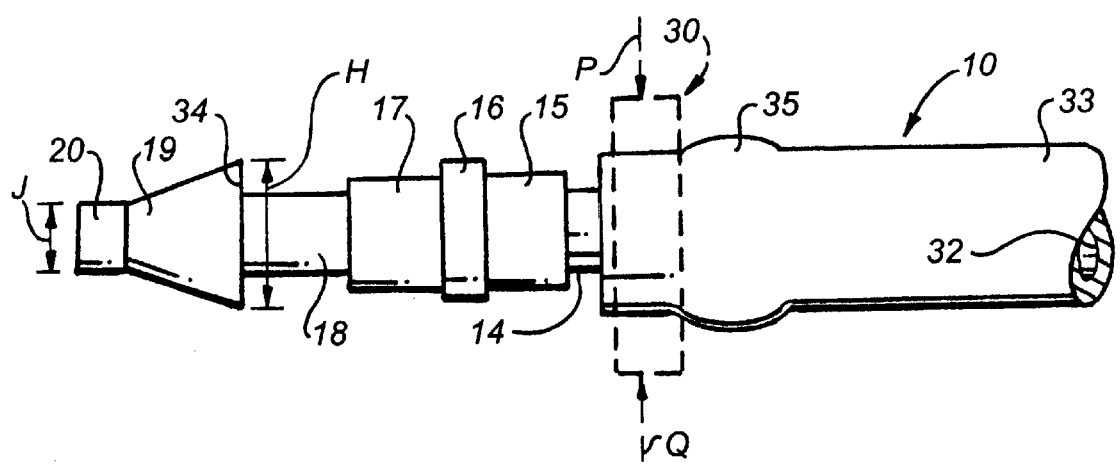
FIG. 2 is a side view illustrating the drip irrigation components of the invention assembled.

In use, member 30 is rolled, slid or otherwise installed on one end of tubing 10 at the position illustrated by dashed lines 30 in FIG. 1. The end of tubing 10 is then slidably forced over connector 50 to the position shown in FIG. 2. The user utilizes his fingers to roll member 30 along tubing 10 past member 13 to the position shown by dashed lines 30 in FIG. 2. In FIG. 2, member 30 is positioned to the left of member 30. If desired, member 30 can be positioned on tubing just to the right of member 30 so that member 30 presses tubing 10 against the outer cylindrical surface of tip 11. If member 30 is at the proper position on tubing 10, it may not be necessary to move member 30 after the end of tubing 10 is slid over connector 50 (or connector 51), i.e., after the end of tubing 10 is slid over connector 50, member 30 may be at the position shown in FIG. 2 and may not have to be moved.

Positioning member 30 on tubing 10 around member 14 is preferred because member 30 tends to "drawn down" tubing 10 over edge 38 and to prevent tubing from being pulled off member 13 and off connector 50.

Having described my invention in such terms as to enable those of skill in the art to make and practice it, and having described the presently preferred embodiments thereof, I claim:

1. A method for assembling a drip irrigation system, comprising the steps of
   (a) providing a length of elastic hollow pliable drip irrigation tubing having first and second ends and an inner cylindrical surface having a selected inner diameter along said length of said tubing and having an outer cylindrical surface having a selected outer diameter;
   (b) providing a hollow drip irrigation member including at least a first end and a second end, said first end of said member including a connector, said connector being shaped and dimensioned to include
      (i) a first outer portion (38) having a width greater than said inner diameter of said tubing to expand said inner cylindrical surface of said tubing to a width greater than said inner diameter when said inner cylindrical surface is slidably forced over said connector, and
      (ii) a second inner portion (14) adjacent said first outer portion and having a width less than the width of said first outer portion;
   (c) providing an O-ring having a durometer in the range of ten to forty and having a circular opening formed therethrough, said opening having a width less than said outer diameter such that when said tubing is inserted through said opening, said tubing elastically expands said opening and generates frictional forces between said O-ring and said tubing which impede sliding said O-ring along said tubing, said O-ring being shaped to roll along said tubing when said O-ring is bowed and pushed along said tubing;
   (d) inserting said first end of said tubing through said opening of said O-ring to mount said O-ring on said tubing at a position inwardly away from said first end;
   (e) slidably forcing said inner cylindrical surface of said first end of said tubing over said first outer portion to a position circumscribing said second inner portion; and,
   (f) pressing against said O-ring to bow said O-ring and roll said O-ring along said tubing to a position on said first end circumscribing said second inner portion.

2. A method for assembling a drip irrigation system, comprising the steps of
   (a) providing a length of elastic hollow pliable drip irrigation tubing having first and second ends and an inner cylindrical surface having an initial selected inner diameter along said length of said tubing and having an outer cylindrical surface having an initial selected outer diameter;
   (b) providing a hollow drip irrigation member including at least a first end and a second end, said first end of said member including a connector, said connector being shaped and dimensioned to include
      (i) a first outer portion (38) having a width greater than said inner diameter of said tubing to expand said inner cylindrical surface of said tubing to a width greater than said inner diameter when said inner cylindrical surface is slidably forced over said connector, and
      (ii) a second inner portion (14) adjacent said first outer portion, having a width less than the width of said first outer portion, and shaped and dimensioned such that when said tubing is slidably inserted over said second inner portion and after passing over said first outer portion, said outer cylindrical surface has said initial selected outer diameter;
   (c) providing an elastic O-ring having a durometer in the range of ten to forty and having a circular opening formed therethrough, said opening having a width less than said outer diameter such that when said tubing is inserted through said opening, said tubing elastically expands said opening and generates frictional forces between said O-ring and said tubing which impede sliding said O-ring along said tubing, said O-ring being shaped to roll along said tubing when said O-ring is bowed and pushed along said tubing;
   (d) inserting said first end of said tubing through said opening of said O-ring to mount said O-ring on said tubing at a position inwardly away from said first end;
   (e) slidably forcing said inner cylindrical surface of first end of said tubing over said first outer portion to a position circumscribing said second inner portion; and,
   (f) pressing against said O-ring to bow said O-ring and roll said O-ring along said tubing to a position on said first end circumscribing said second inner portion.

* * * * *